(12) United States Patent  
Olson et al.

(10) Patent No.: US 7,654,843 B2
(45) Date of Patent: Feb. 2, 2010

(54) CONNECTOR ASSEMBLY WITH INTERNAL SEALS AND MANUFACTURING METHOD

(75) Inventors: Thomas J. Olson, Eagan, MN (US); Andrew J. Ries, Lino Lakes, MN (US); George Patras, Greenfield, MN (US); John D. Longtin, Lake Elmo, MN (US)

(73) Assignee: Medtronic, Inc., Minneaoplis, MN (US)

( * ) Notice: Subject to any disclaimer, the term of this patent is extended or adjusted under 35 U.S.C. 154(b) by 0 days.

(21) Appl. No.: 11/363,651

(22) Filed: Feb. 28, 2006

(65) Prior Publication Data

US 2007/0202728 A1 Aug. 30, 2007

(51) Int. Cl.
*H01R 13/64* (2006.01)

(52) U.S. Cl. .................. 439/248; 607/115

(58) Field of Classification Search ........... 439/736, 439/248, 909, 843, 523, 668, 699.1, 931, 439/933, 927, 827, 669, 387, 578–585; 607/115, 607/36, 37, 377, 378
See application file for complete search history.

(56) References Cited

U.S. PATENT DOCUMENTS

| 4,226,244 | A | 10/1980 | Coury et al. |
|---|---|---|---|
| 4,934,367 | A | 6/1990 | Daglow et al. |
| 4,971,057 | A | 11/1990 | Theres |
| 5,070,605 | A | 12/1991 | Daglow et al. |
| 5,076,270 | A | 12/1991 | Stutz, Jr. |
| 5,431,695 | A | 7/1995 | Wiklund et al. |
| 6,574,508 | B2 | 6/2003 | Zaouali et al. |
| 6,817,905 | B2 | 11/2004 | Zart et al. |
| 7,083,474 | B1 | 8/2006 | Fleck et al. |
| 7,133,722 | B2 * | 11/2006 | Hansen et al. ............ 607/37 |
| 7,164,951 | B2 * | 1/2007 | Ries et al. ............... 607/37 |
| 7,167,749 | B2 * | 1/2007 | Biggs et al. ............. 607/36 |
| 7,195,523 | B2 * | 3/2007 | Naviaux ............... 439/827 |
| 2002/0143376 | A1 * | 10/2002 | Chinn et al. ............ 607/115 |
| 2003/0163171 | A1 | 8/2003 | Kast |
| 2004/0122481 | A1 | 6/2004 | Tidemand et al. |
| 2005/0033138 | A1 | 2/2005 | Ries et al. |
| 2005/0137642 | A1 | 6/2005 | Zart et al. |
| 2005/0149140 | A1 | 7/2005 | Hansen et al. |

* cited by examiner

*Primary Examiner*—Edwin A. León
(74) *Attorney, Agent, or Firm*—Carol F. Barry (57) ABSTRACT

A medical device connector assembly and fabrication method are provided wherein the connector assembly includes a core element, a plurality of conductive members positioned along the core element, and a plurality of sealing members positioned between the conductive members, the sealing members having an outer surface supported by the core element.

40 Claims, 9 Drawing Sheets

CONNECTOR ASSEMBLY WITH INTERNAL SEALS AND MANUFACTURING METHOD

TECHNICAL FIELD

The invention relates generally to implantable medical device connector assemblies and in particular to a device connector assembly including internal seals and an associated method of manufacture

BACKGROUND

Electrical connectors and other similar electrical components often include electrical conductors embedded within an insulating block to isolate the conductor from the surrounding environment. Embedding the conductor within a block protects the conductor from damage, and also prevents the delivery of an unintended electrical shock. Electrical isolation is particularly important when the connector is to be coupled to an implantable medical device such as a pacemaker or defibrillation system. Electrical connector assemblies are coupled to a hermetically sealed housing of an implantable medical device that encloses internal circuitry such as a hybrid circuit board and one or more batteries. Such a medical device connector assembly is adapted for receiving medical leads used with the implantable medical device.

Methods for forming electrical connector assemblies having conductors embedded within an insulating block may include injection molding techniques or thermoset casting techniques. An improved method for forming an implantable medical device connector assembly with embedded conductors is generally disclosed in U.S. Pat. No. 6,817,905 (Zart et al.), hereby incorporated herein by reference in its entirety. The method generally includes forming a core portion using either an injection molding process or a machining process. The core portion is fitted with electrically conductive components and submitted to a subsequent overmold process in which a second shot of thermoplastic material is injected into the mold. This improved process allows complex connector structures to be manufactured in a fast production cycle.

In the implantable medical device industry, standards have been developed for lead connector assemblies which are adapted to mate with the device connector assembly. In past practice, lead connector assemblies have included sealing members positioned around insulating structures located between lead connector terminals. The sealing members prevent the ingress of body fluids into a connector bore thereby electrically isolating the connector circuit elements. Ingress of body fluids may otherwise lead to a short circuit between separate connector circuits.

A new lead connector assembly industry standard, the IS4 connector assembly, includes four in-line lead terminals that are separated by insulating structures but do not include sealing members. A device connector assembly adapted to receive the IS4 lead connector assembly should therefore incorporate sealing members to provide electrical isolation of the connector circuits. Such sealing members are typically formed as rings fabricated from a supple, biocompatible material, such as silicone rubber. The sealing members are adapted to mate with insulating structures of the IS4 lead connector assembly to form a fluid-resistant seal.

The supple sealing members, however, may not withstand high pressure or high temperature processes which may be used during manufacture of the connector assembly, such as the overmolding process disclosed in the '905 Zart patent. A device connector assembly that incorporates sealing members for accommodating lead connectors without sealing members and withstands high pressure and/or high temperature manufacturing processes without compromising the integrity of the connector assembly is therefore needed.

DETAILED DESCRIPTION

In the following description, references are made to illustrative embodiments for carrying out the invention. It is understood that other embodiments may be utilized without departing from the scope of the invention.

Figure 1:
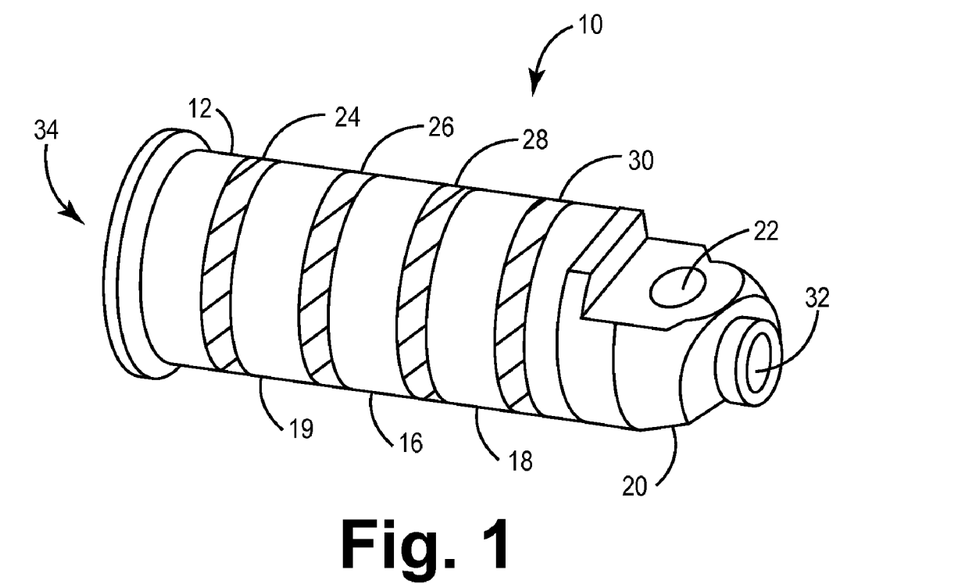
FIG. 1 is a perspective view of a stacked subassembly of conductive members separated by sealing members for use in a core element of a device connector assembly.

FIG. 1 is a perspective view of a stacked subassembly of conductive members separated by sealing members. Stacked subassembly 10 is used in forming a core element included in an implantable medical device connector assembly according to one embodiment of the invention. Stacked subassembly 10 includes an end cap 12, three connectors 14, 16, and 18, and a set screw block 20, separated by sealing members 24, 26, 28 and 30. Set screw block 20 includes an open end aperture 32 through which a pin connector of a lead connector assembly may be inserted. Set screw block 20 further includes a set screw aperture 22 for receiving a set screw used for securing the pin connector of a lead connector assembly and retain the lead connector assembly within a connector bore formed by stacked subassembly 10. Set screw block 20 serves as a connector for making electrical contact with the pin connector of a lead connector assembly. The connectors 14, 16, and 18 may be embodied as multi-beam contacts, spring contacts, or any other electrical contacts for making electrical connection with lead connector terminals that become aligned with connectors 14, 16, and 18 when the lead connector assembly is fully inserted into stacked subassembly 10. End cap 12 is provided with an open receptacle 34 for receiving a lead connector assembly and acts to terminate the stack.

Sealing members 24, 26, 28 and 30 are fabricated from an insulating material to electrically isolate connectors 14, 16, 18 and set screw block 20. Sealing members 24, 26, 28 and 30 are typically formed of a compliant material, such as a medical grade silicone rubber, such that sealing members 24, 26, 28 and 30 form a fluid-resistant seal with insulating structures of a lead connector assembly. When the lead connector assembly is fully inserted into stacked subassembly 10, sealing members 24, 26, 28, and 30 will be aligned with insulating structures separating lead connector assembly terminals. Sealing members 24, 26, 28 and 30 will form a fluid-resistant interface with the insulating structures of the lead connector assembly.

Figure 2:
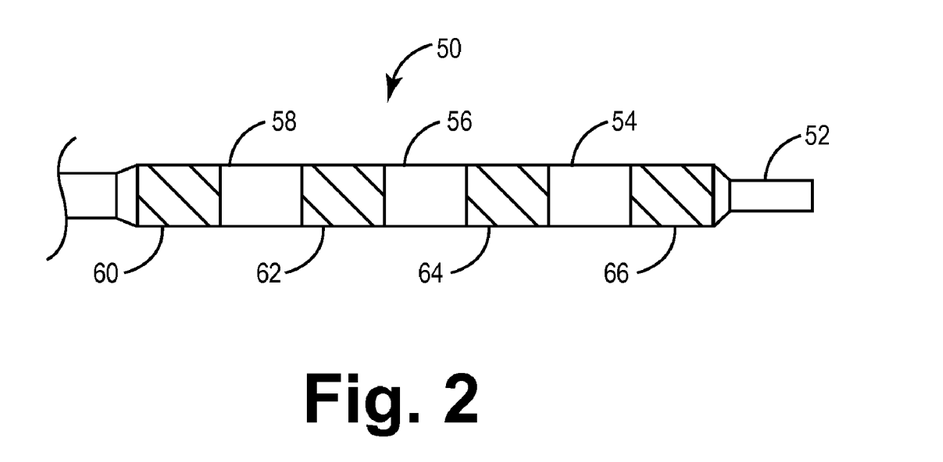
FIG. 2 is a plan view of a proximal lead connector assembly adapted for use with the stacked subassembly of FIG. 1.

FIG. 2 is a plan view of a proximal lead connector assembly adapted for use with the stacked subassembly of FIG. 1. Lead connector assembly includes a pin connector terminal 52 and three ring connector terminals 54, 56, and 58. Each of terminals 52, 54, 56, and 58 are electrically coupled to respective insulated conductors extending through an elongated lead body to electrodes generally positioned along the distal end of the lead body. The terminals 52, 54, 56, and 58 are separated and electrically isolated from one another by insulating structures 60, 62, 64, and 66. Lead connector assembly 50 is commonly referred to as an "in-line" connector assembly in contrast to bifurcated connector assemblies which carry connector terminals on separate branches. In past practice, in-line lead connector assemblies typically have included sealing rings along the insulating structures between connector terminals for providing a fluid resistant seal between circuit elements when the lead connector assembly is coupled to an implanted device. Lead connector assembly 50 does not include such sealing rings. Lead connector assembly 50 may generally correspond to IS4 lead connector assembly, though the present invention is not limited to embodiments corresponding only to the IS4 architecture. Embodiments of the invention include device connector assemblies adapted to receive any in-line lead connector assembly, particularly in-line lead connector assemblies that do not incorporate sealing rings.

Figure 3:
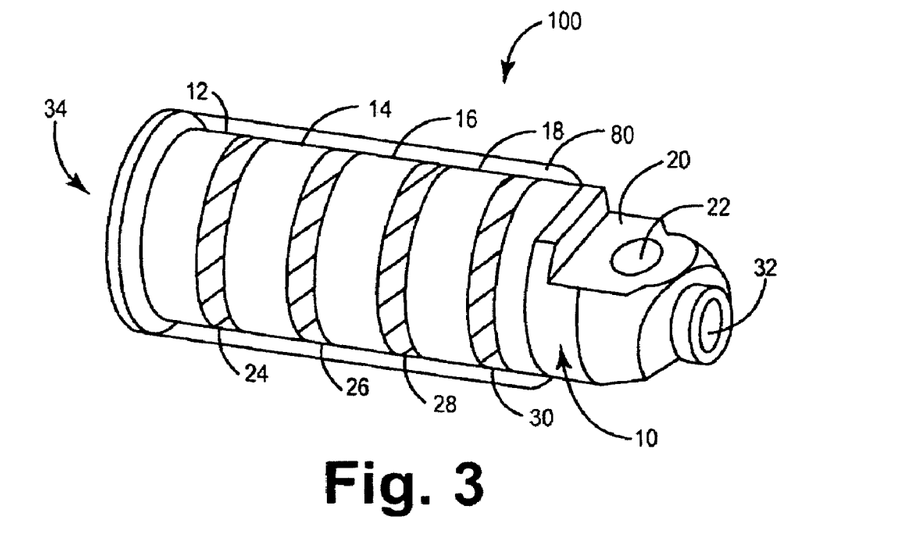
FIG. 3 is a perspective view of a core element for use in a device connector assembly according to one embodiment of the invention.

FIG. 3 is a perspective view of a core element for use in a device connector assembly according to one embodiment of the invention. Core element 80 is formed during a casting or molding process to encapsulate at least a portion of stacked subassembly 10. Core element 80 is formed from an adhesive, such as epoxy or another thermoset material, and is shown to be transparent in FIG. 3 for the sake of illustration. Connector bore assembly 100 may be fabricated by loading stacked subassembly 10 on a mandrel (not shown) and positioning stacked subassembly 10 in a mold into which the core element material is applied. The stacked subassembly components may be held in position during the molding or casting process by the mandrel. Core element 80 is formed in a low pressure, low temperature casting process and acts to provide external support to sealing members 24, 26, 28 and 30 during subsequent manufacturing processes. Subsequent manufacturing processes may involve pressures and/or temperatures that would compromise the structural integrity of sealing members 24, 26, 28 and 30 if applied directly thereto without the external support of core element 80. As such, the material selected for forming core element 80 is generally an adhesive, including thermoset materials such as an epoxy, which can be cured under low pressure and low temperature conditions to a stronger form which provides the external support to sealing members 24 through 30 needed during subsequent manufacturing processes. Core element 80 may further act to retain the stacked components of subassembly 10 in stable positions with respect to one another.

Figure 4:
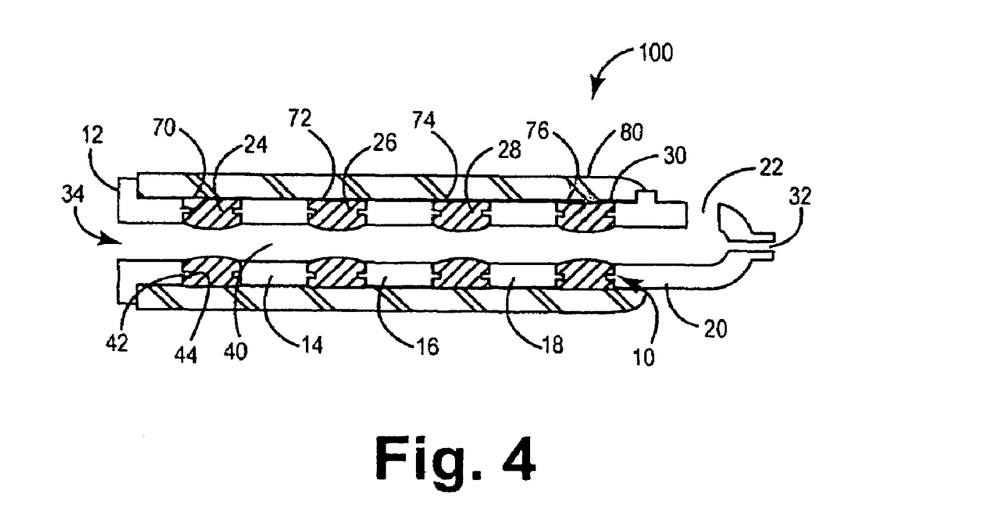
FIG. 4 is a side sectional view of the core element of FIG. 3.

FIG. 4 is a side sectional view of connector bore assembly 100. Stacked subassembly 10 forms a central bore 40 having an open receptacle 34 formed by end cap 12. Central bore 40 is adapted to receive a lead connector assembly such as the lead connector assembly 50 shown in FIG. 2. Each of sealing members 24, 26, 28, and 30 have an outer surface 70, 72, 74, 76 supported by core element 80. Core element 80 provides external support to sealing members 24 through 30 during subsequent manufacturing processes used in forming the final device connector assembly. Internal support may be provided, if needed, to sealing members 24 through 30 by inserting a mandrel through bore 40 during manufacturing procedures.

As shown in FIG. 4, stacked components may include interlocking interfacing structures for stabilizing the positions of stacked components during the manufacturing process. In the depicted embodiment, end cap 12 is shown having a flange 42 that mates with a groove 44 provided on sealing member 24. Such tongue-in-groove structures are shown at each interface between a sealing member and an adjacent component. Other configurations for mechanically interfacing or interlocking adjacent components in stacked subassembly 10 may be used.

Figure 5:
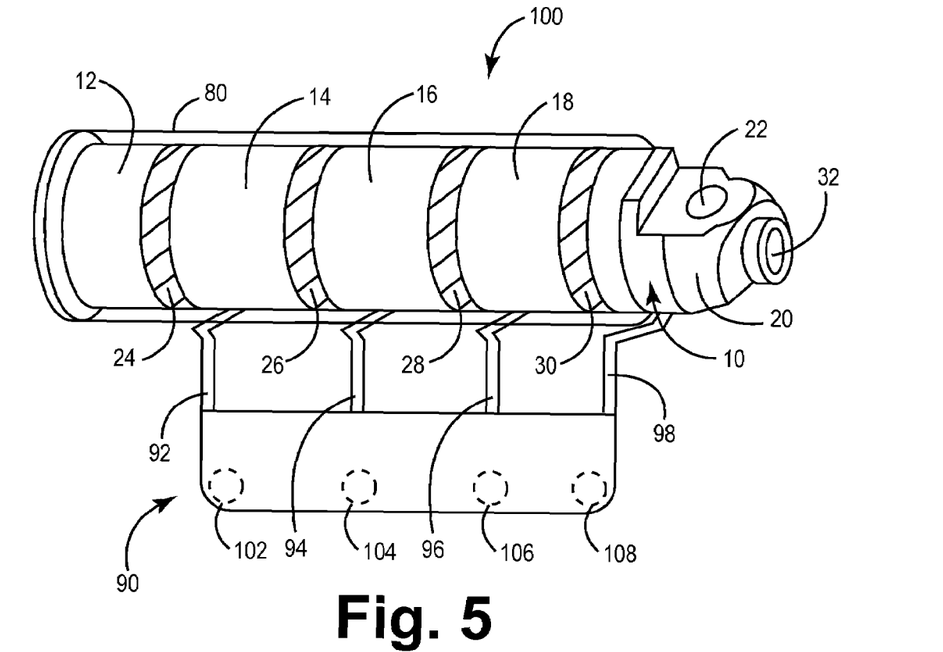
FIG. 5 is a perspective view of the core element of FIG. 4 coupled to a circuit member 90.

FIG. 5 is a perspective view of the core element of FIG. 4 coupled to a circuit member 90. Circuit member 90 includes multiple conductive traces 92, 94, 96, and 98, each extending to a respective connector pad 102, 104, 106, and 108. Connector pads 102 through 108 are used to electrically couple traces 92 through 98 to circuitry enclosed in an implantable medical device housing. Individual traces 92 through 98 are electrically coupled to respective conductive components, i.e., set screw block 20 and connectors 14, 16, and 18, included in stacked subassembly 10. Electrical connection is made between traces 92 through 98 and conductive components 14 through 20, for example, by soldering or welding.

In one assembly method, stacked subassembly 10 is assembled, and circuit element 90 is welded to conductive components included in stacked subassembly 10. The stacked subassembly 10 with circuit element 90 already electrically coupled thereto, is placed in a mold. Core element 80 is then formed in a low pressure, low temperature casting procedure.

Figure 6:
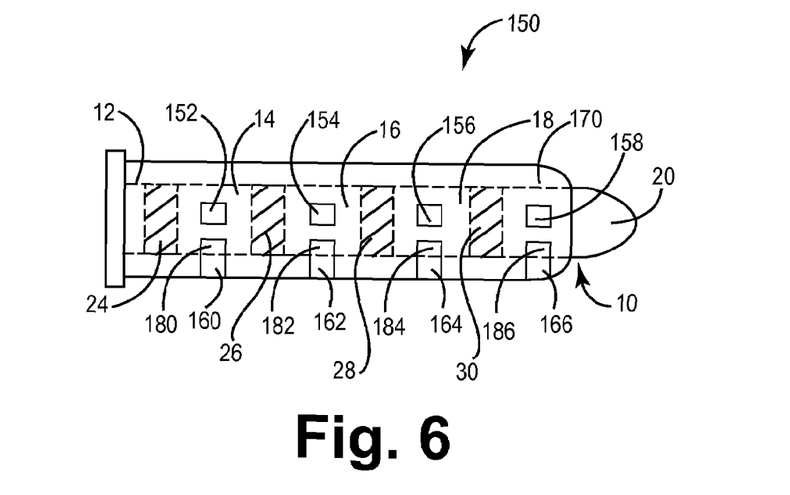
FIG. 6 is a bottom plan view of an alternative embodiment of a core element for use in a connector assembly.

FIG. 6 is a bottom plan view of an alternative embodiment of a core element for use in a connector assembly. Core element 170 is formed with multiple apertures 180 through 186 for receiving individual traces of a circuit element, such as circuit element 90 as shown in FIG. 5. Core element 170 may further include positioning structures 160 through 166, such as grooves or channels, to facilitate alignment of circuit element traces with apertures 180 through 186. Core element 170 further includes windows 152 through 158 positioned over each of the conductive components 14, 16, 18 and 20 included in stacked subassembly 10. Windows 152 through 158 provide access to the conductive components 14 through 20 after core element 170 is formed, to allow welding or other electrical coupling methods to be applied to conductive components 14 through 20 and respective traces included in a circuit element.

In an alternative assembly method, stacked subassembly 10 is positioned in a mold, and core element 170 is formed in a low pressure, low temperature casting procedure to encapsulate at least a portion of stacked subassembly 10. Core element 170 is formed with windows 152 through 158, apertures 180 through 186 and positioning structures 160 through 166 during the casting process. After core element 170 has cured, individual traces of a circuit element, such as circuit element 90 shown in FIG. 5, are positioned along positioning structures 160 through 166 and inserted through apertures 180 through 186 until they are positioned over respective conductive elements 14 through 20 through windows 152 through 158. The individual traces are then welded to respective conductive components 14 through 20 through windows 152 through 158. The connector bore assembly 150 is then ready for an overmolding process or other high pressure and/or high temperature processes used in fabricating the final connector assembly.

Figure 7:
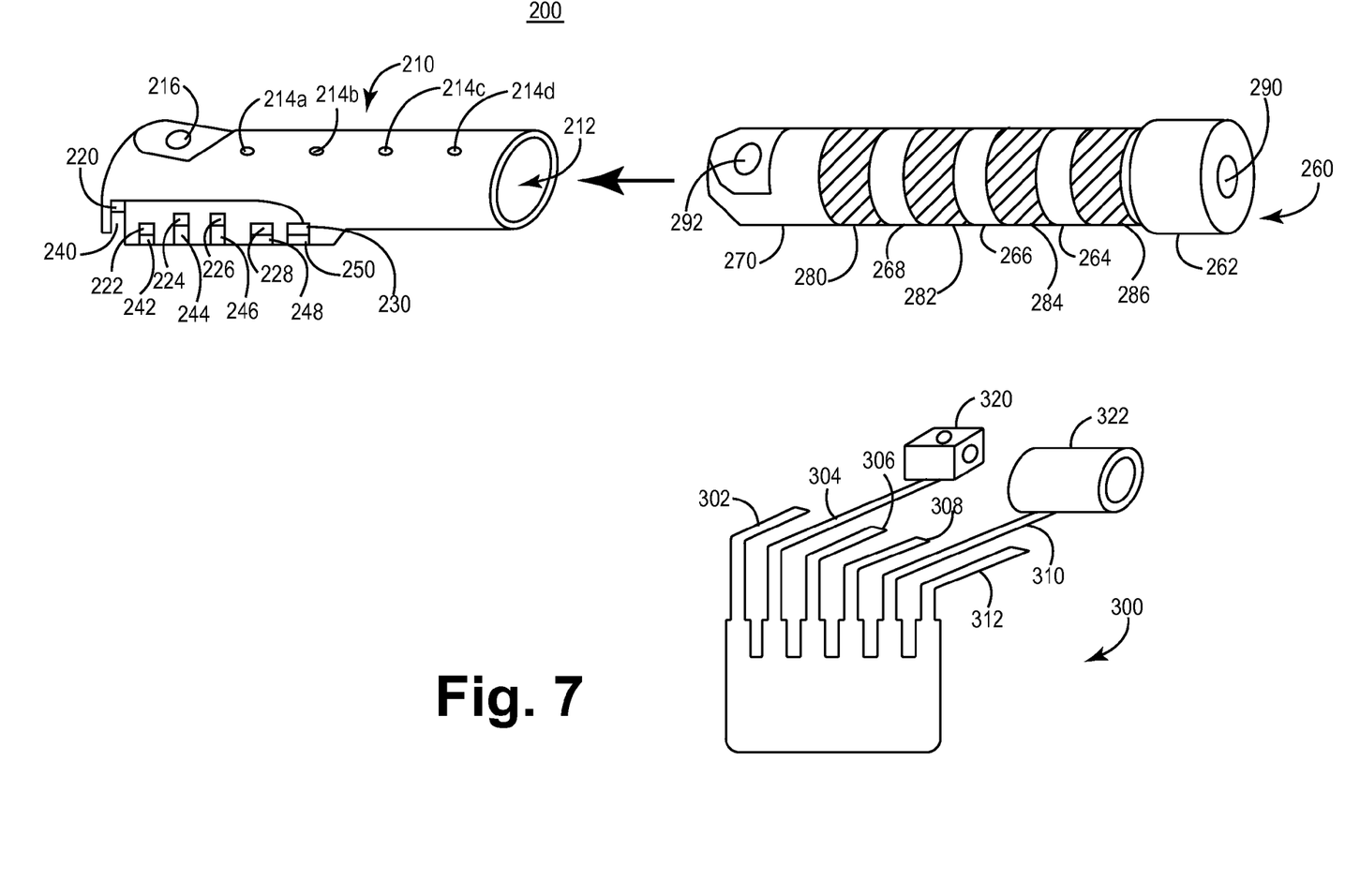
FIG. 7 is an exploded, perspective view of an alternative embodiment of a core element for use in a device connector assembly.

FIG. 7 is an exploded, perspective view of an alternative embodiment of a core element for use in a device connector assembly. The core element 200 includes a rigid plastic sleeve 210 forming a lumen 212 adapted for receiving stacked subassembly 260. Stacked subassembly 260 includes end cap 262 and conductive components 264, 266, 268, and 270 stacked with intervening sealing members 280 through 286. For example, stacked subassembly 260 includes a set screw block 270 and connectors 264, 266 and 268. End cap 262 is provided with an open receptacle 290 for receiving a lead connector assembly as described previously.

Sleeve 210 may be fabricated by injection molding a thermoplastic material such as polyurethane. Sleeve 210 includes a set screw aperture 216 which becomes aligned with the set screw aperture 292 of set screw block 270 when stacked subassembly 260 is inserted in sleeve 210 through lumen 212. Sleeve 210 includes at least one fill port 214 through which an adhesive, such as epoxy or another thermoset material, is applied to fill sleeve 210 after stacked subassembly 260 has been positioned within sleeve 210.

Sleeve 210 may further include structures for accommodating a circuit element 300. Circuit element 300 includes multiple traces 302 through 312 adapted for electrical coupling to the conductive components 264 through 270 of stacked subassembly 260 and any other conductive components to be included in a device connector assembly. Core element 200 may be included in a multi-bore connector assembly in which additional connector bores are formed by conductive elements such as set screw blocks, spring connectors, or multi-beam connectors. It is recognized that one or more core elements providing support to sealing members may also be included in a device connector assembly.

In the example shown, circuit element 300 includes a trace 304 electrically coupled to a set screw block 320 and trace 310 electrically coupled to a multi-beam connector 322. Set screw block 320 and multi-beam connector 322 will be positioned along a second connector bore in the final device connector assembly after an overmolding process is performed as will be described below.

Sleeve 210 is shown having positioning structures 240 through 250 for aligning and retaining traces 302 through 312. Traces 302 through 312 are aligned with and will extend through apertures 220 through 230. Traces 302 through 312 are electrically coupled to respective conductive components, for example by welding or soldering. Traces 302, 306, 308 and 312 may be welded to conductive components 264 through 270 of stacked subassembly 260 through windows provided along the bottom side of sleeve 210 (not visible in the perspective view of FIG. 7). Such windows provide access for forming a weld joint or other electrical coupling between traces and conductive components as generally described in conjunction with FIG. 6.

In an assembly method, stacked subassembly 260 is inserted into sleeve 210. Circuit element traces 302 through 312 are positioned along positioning structures 240 through 248 and advanced through apertures 220 through 230. Traces 302, 304, 308, and 312 are welded to conductive components 270, 268, 266, and 264, respectively, through windows provided along the bottom side of sleeve 210. The core element material is then injected through fill ports 214a through 214d to encapsulate the outer surfaces of sealing members 280 through 286 included in stacked subassembly 260.

Figure 8:
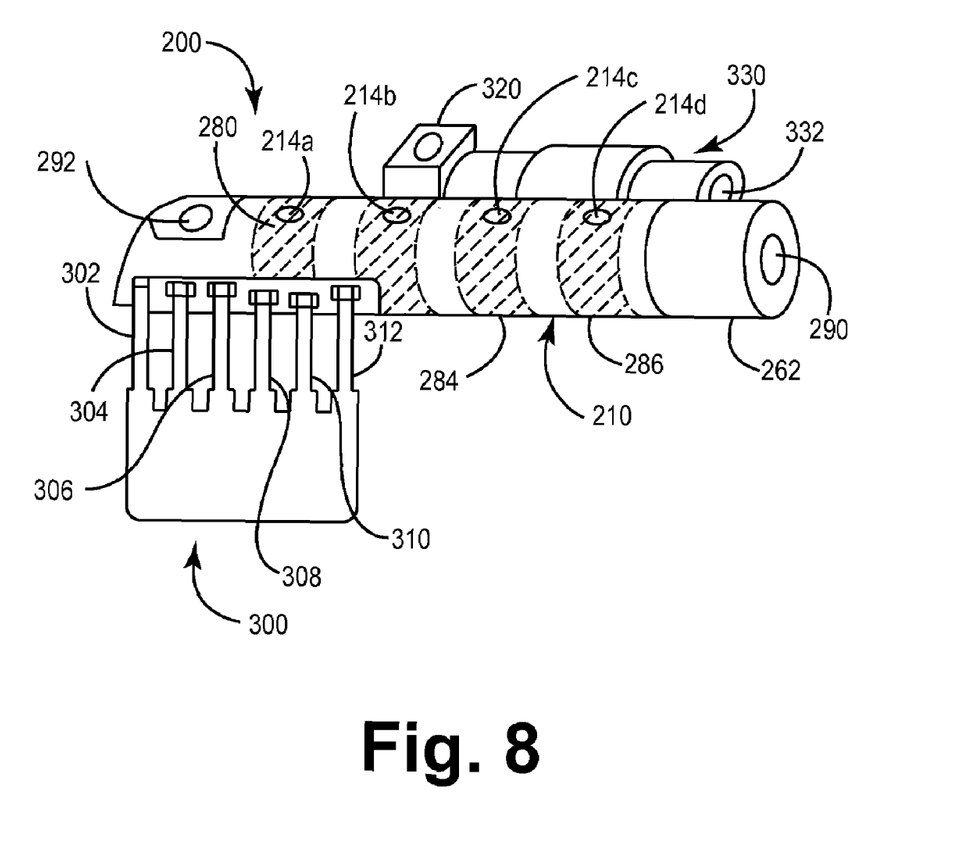
FIG. 8 is a perspective view of the assembled core element shown in FIG. 7.

FIG. 8 is a perspective view of the assembled core element 200. Core element 200 includes sleeve 210 in which the stacked subassembly 260 (shown in FIG. 7) has been inserted. An adhesive, such as epoxy or another thermoset material, has been injected through fill ports 214a through 214d to fill plastic sleeve 210 and encapsulate the outer surface of stacked subassembly 260 at least along the outer surfaces of sealing members 280 through 286. The filled sleeve 210 provides exterior support to sealing members 280 through 286 during subsequent high pressure and/or high temperature manufacturing processes. Traces 302 through 312 of circuit element 300 are aligned along positioning structures and extend through apertures included in sleeve 210 (shown previously in FIG. 6). Core element 200 and the conductive components and sealing members positioned therein form a connector bore for receiving an in-line lead connector assembly via receptacle 290. A second core element 330 is shown formed over the multi-beam contact 322 (shown in FIG. 6) and at least a portion of set screw block 320 to form a second connector bore 332.

Figure 9:
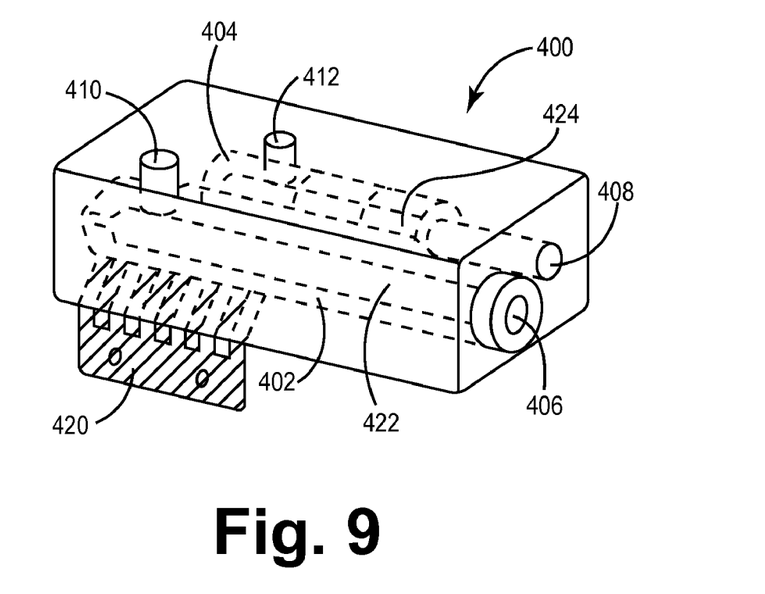
FIG. 9 is a perspective view of a device connector assembly including a core element according to one embodiment of the invention.

FIG. 9 is a perspective view of a device connector assembly including a core element according to one embodiment of the invention. Connector assembly 400 is formed during an overmolding process to encapsulate core element 402 and a portion of circuit member 420. Core element 402 provides external support to sealing members included in a stacked subassembly as described previously. The overmolding process generally involves loading the core element 402, with circuit element 420 appropriately coupled thereto, into a mold assembly and injecting a thermoplastic material into the mold. Reference is made to the above-incorporated '905 Zart patent for an appropriate overmolding process that may be used to form connector assembly 400. Connector assembly 400 includes a receptacle 406 for receiving a lead connector assembly when it is advanced into connector bore 422, indicated by dash-dot line, inside core element 402. Connector assembly 400 may further include one or more additional receptacles for receiving additional leads in one or more additional connector bores. In the example shown, connector assembly 400 includes a second receptacle 408 for receiving a lead inserted into a second connector bore 424.

Connector assembly 400 includes a set screw aperture 410 for receiving a set screw advanced into a set screw block positioned along core element 402. Connector assembly 400 may include additional set screw apertures 412 as needed for receiving additional set screws used for securing lead connector assemblies positioned in other connector bores 424.

Figure 10:
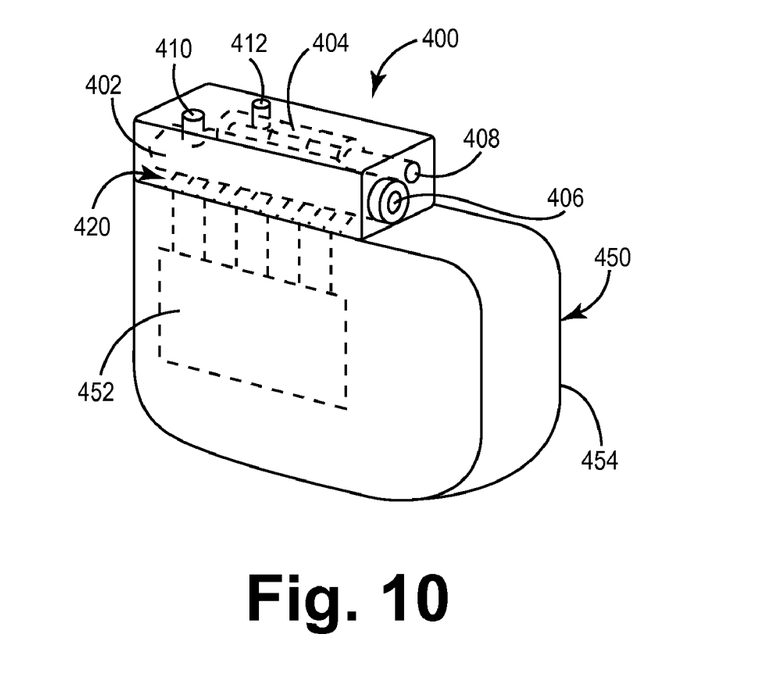
FIG. 10 is a perspective view of a completed connector assembly coupled to an implantable medical device.

FIG. 10 is a perspective view of completed connector assembly 400 coupled to an implantable medical device 450. Implantable medical device (IMD) 450 may be a pacemaker, cardioverter/defibrillator, neurological stimulator, physiological monitor, or any other implantable medical device utilizing medical leads. In particular, sealing members are provided along a core element 402 for creating a fluid-resistant seal with insulating portions of a lead connector assembly inserted into receptacle 406. Circuit element 420, partially encapsulated in connector assembly 400 is connected to internal circuitry 452 enclosed in IMD housing 454. Electrical connection between IMD internal circuitry 452 and circuit element 42 is typically made via a feedthrough array extending through hermetically sealed housing 454.

Figure 11:
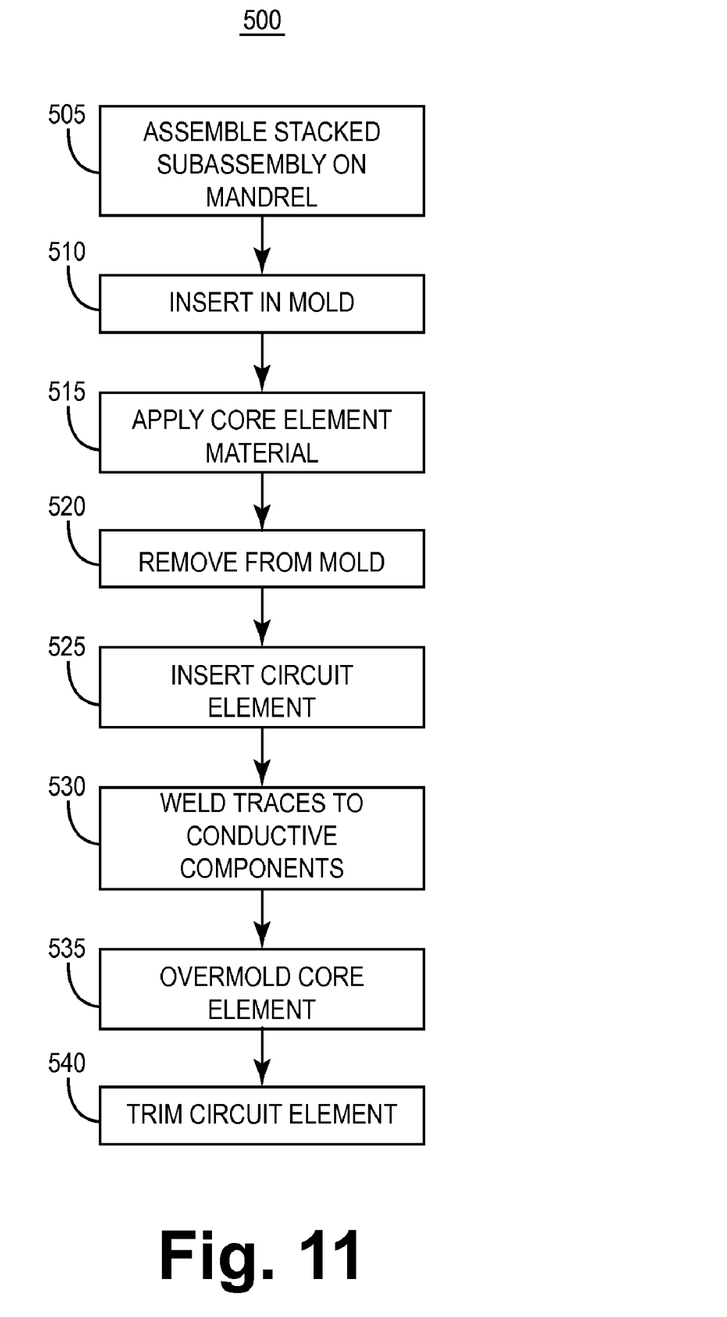
FIG. 11 is a flow chart summarizing steps included in a method for fabricating a connector assembly.

FIG. 11 is a flow chart summarizing steps included in a method for fabricating a connector assembly. At block 505, a stacked subassembly including conductive components separated by sealing members is assembled on a mandrel. At block 510 the stacked subassembly is placed in a mold, and a thermoset material is applied in a low pressure, low temperature casting process to form a core element around at least a portion of the stacked subassembly, including at least the sealing members. At block 520, the core element is removed from the mold after curing. The mold used to form the core element includes structures for forming circuit element positioning structures and/or apertures and welding windows in the core element. Individual traces of a circuit element are positioned along positioning structures, if provided, and advanced through apertures and alongside respective conductive components included in the stacked subassembly at block 525. At block 530, the individual traces are welded to the respective conductive components through the windows.

The core element is then prepared for an overmolding process for fabricating the final connector assembly. The core element and any other conductor assembly components are placed into a mold and a thermoplastic material is injected into the mold at block 535. The core element is overmolded to form the final connector assembly in a high-pressure and/or high temperature process. At block 540, the circuit element is trimmed to separate and electrically isolate individual circuits to be included in the final connector assembly.

Figure 12:
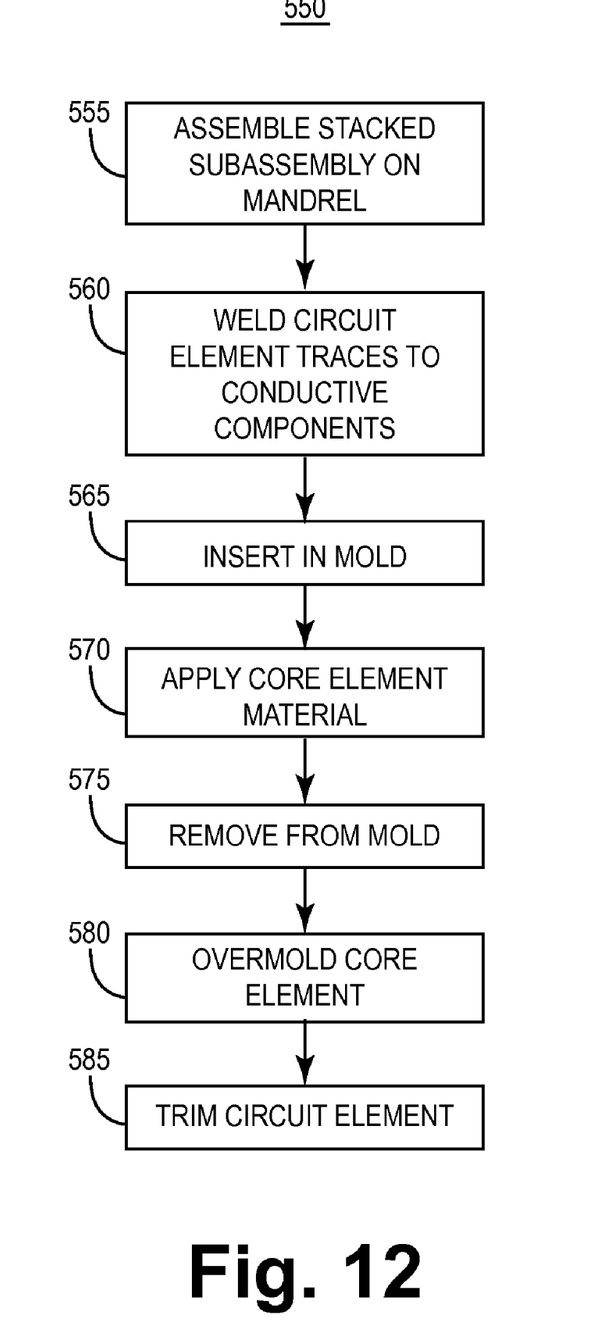
FIG. 12 is a flow chart summarizing steps included in an alternative method for fabricating a connector assembly.

FIG. 12 is a flow chart summarizing steps included in an alternative method for fabricating a connector assembly. At block 555, a stacked subassembly including conductive components separated by sealing members is assembled on a mandrel. Circuit element traces are welded or otherwise electrically coupled to the conductive components at block 560. The stacked subassembly is then inserted into a mold and the core element material is applied in a low pressure, low temperature casting procedure to form a core element around at least a portion of the stacked subassembly, including at least the sealing members. After the core element material has cured, the core element is removed form the mold at block 575. The core element is then prepared for an overmolding process. At block 580, the core element is overmolded to form the final connector assembly as described above. The circuit element is trimmed at block 585 to separate and electrically isolate individual circuits to be included in the final connector assembly.

Figure 13:
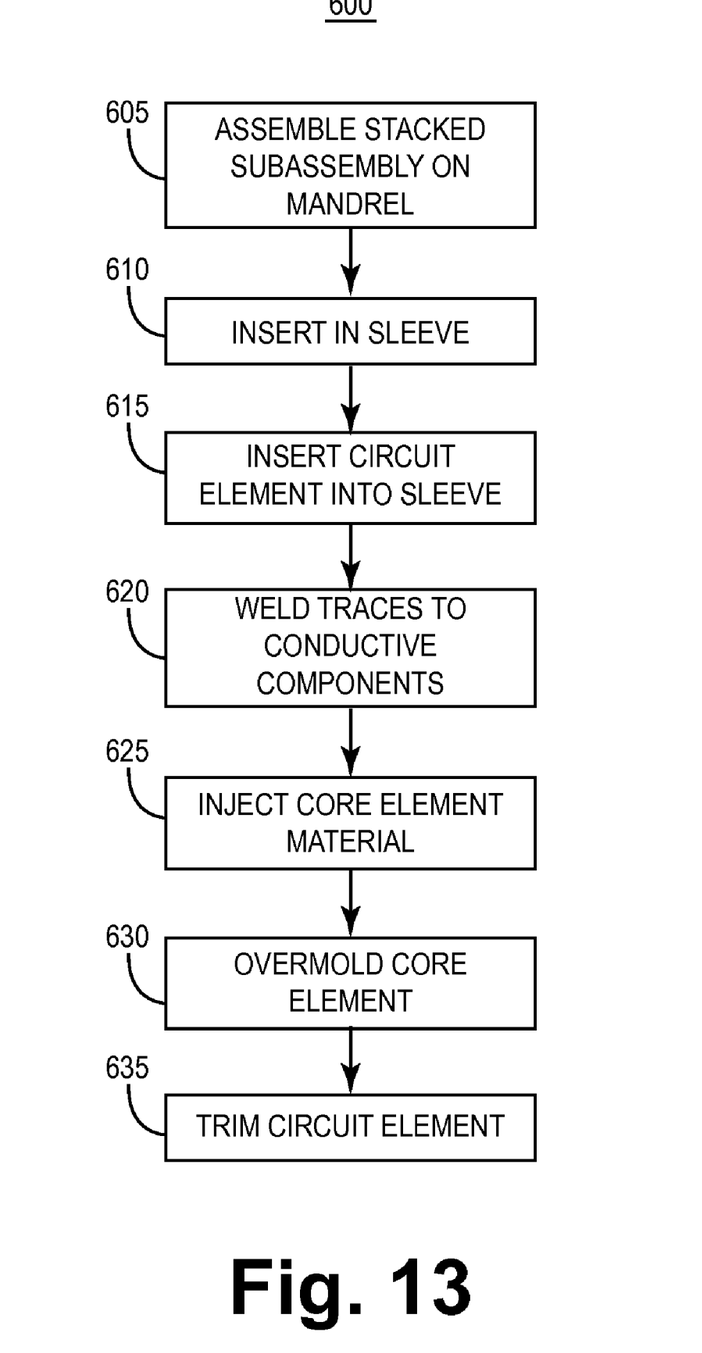
FIG. 13 is a flow chart summarizing steps included in yet another embodiment of a method for fabricating a connector assembly.

FIG. 13 is a flow chart summarizing steps included in yet another embodiment of a method for fabricating a connector assembly. At block 605, a stacked subassembly including conductive components separated by sealing members is assembled on a mandrel. The stacked subassembly is then inserted into a rigid plastic sleeve at block 610. The plastic sleeve includes apertures for receiving individual traces of a circuit element as described previously in conjunction with FIG. 7. At block 615, the individual traces of a circuit element are inserted through the apertures and advanced alongside a respective conductive component included in the stacked subassembly. At block 620, the individual traces are electrically coupled to the conductive components, for example by welding through windows provided in the sleeve.

At block 625, the selected core element material is injected into the sleeve through one or more fill ports to form the core element and encapsulate at least the sealing members of the stacked subassembly. After the core element material has cured, the core element is prepared for an overmolding process. At block 630, the core element is overmolded to form the final connector assembly as described previously. The circuit element is trimmed at block 635 to separate and electrically isolate individual circuits to be included in the final connector assembly.

Thus, a connector assembly incorporating sealing members and method of fabricating the same have been presented in the foregoing description with reference to specific embodiments. It is appreciated that various modifications to the referenced embodiments may be made without departing from the scope of the invention as set forth in the following claims.

The invention claimed is:

1. An implantable medical device connector assembly, comprising:
   a core element having an interior surface;
   a plurality of conductive members positioned along the interior surface of the core element;
   a plurality of sealing members positioned between the conductive members;
   the plurality of sealing members having an outer surface supported by the interior surface of the core element;
   wherein the plurality of conductive members and the plurality of sealing members form a bore;
   an electrically conductive circuit element having a plurality of conductive traces extending through the core element and electrically coupled to the plurality of conductive members; and
   an overmold structure formed from a thermoplastic material, the overmold structure extending over and adhering to the core element and at least a portion of the electrically conductive circuit element.

2. The connector assembly of claim 1 wherein the core element includes a plurality of apertures through which the plurality of conductive traces extend.

3. The connector assembly of claim 1 including a plurality of positioning structures extending along the core element.

4. The connector assembly of claim 1 wherein the core element includes a plurality of windows positioned over the conductive members.

5. The connector assembly of claim 1 wherein the plurality of conductive members and the plurality of sealing members include interlocking interfacing structures.

6. The connector assembly of claim 1 wherein the core element being formed from epoxy.

7. The connector assembly of claim 1 wherein the bore has a diameter sized for receiving an IS4 medical lead connector assembly.

8. The connector assembly of claim 1 wherein the plurality of conductive members and the plurality of sealing members each having an inner surface which inner surfaces together form the bore, the inner surfaces of the sealing members forming a fluid-resistant interface with insulating structures on the medical lead connector assembly.

9. The connector assembly of claim 1 wherein the core element includes a rigid sleeve.

10. The connector assembly of claim 9 wherein the rigid sleeve includes at least one fill port through which a core element material is delivered.

11. A method for manufacturing an implantable medical device connector assembly, comprising:
    stacking a plurality of individual conductive members and a plurality of individual sealing members, the individual sealing members positioned between the individual conductive members to form a stacked subassembly;
    forming a core element along at least a portion of the stacked subassembly including the plurality of individual sealing members;
    electrically coupling conductive traces to the conductive members; and
    overmolding the core element in a thermoplastic material.

12. The method of claim 11 wherein electrically coupling conductive traces to the conductive members includes performing the electrically coupling through windows included in the core element.

13. The method of claim 12 further including inserting the stacked subassembly in a sleeve and wherein forming the core element includes filling the sleeve with an adhesive.

14. The method of claim 11 wherein forming the core element comprises allowing a core element material to cure, the cured core element supporting an outer surface of the sealing members during the overmolding.

15. The method of claim 14 wherein the core element is cured at a first temperature and a first pressure and the overmolding occurs at one of a second temperature greater than the first temperature and a second pressure greater than the first pressure.

16. An implantable medical device connector assembly, comprising:
   a stacked subassembly comprising a plurality of individual conductive members stacked with a plurality of individual sealing members positioned between the conductive members, each of the individual conductive members and each of the individual sealing members having an inner surface and an outer surface, the outer surfaces of the individual conductive members and the outer surfaces of the individual sealing members together forming a stacked subassembly outer surface; and
   a core element having an interior surface extending over the stacked subassembly outer surface,
   the core element interior surface supporting the outer surfaces of the individual sealing members, the core element cast or molded over the outer surfaces of the individual sealing members and the outer surfaces of the individual conductive members, the core element formed from an adhesive that encapsulates the outer surfaces of the individual sealing members and the outer surfaces of the individual conductive members;
   the inner surfaces of the individual conductive members and the inner surfaces of the individual sealing members together forming a central bore for receiving a medical lead connector assembly, the inner surfaces of the individual sealing members forming a fluid-resistant interface with insulating structures of the lead connector assembly.

17. The connector assembly of claim 16 wherein the stacked subassembly further comprises a terminal component stacked with the individual conductive members and the individual sealing members, the terminal component having a receptacle aligned with the bore for receiving the medical lead connector assembly.

18. The connector assembly of claim 16 further comprising an overmold structure formed from a thermoplastic material, the overmold structure extending over and adhering to the core element.

19. An implantable medical device connector assembly, comprising:
   a stacked subassembly comprising
   a plurality of individual conductive members; and
   a plurality of individual sealing members stacked with and positioned between the conductive members to separate the conductive members,
   each of the individual conductive members and each of the individual sealing members having an inner surface and an outer surface,
   the outer surfaces of the individual conductive members and the outer surfaces of the individual sealing members together forming a stacked subassembly outer surface,
   the inner surfaces of the individual conductive members and the inner surfaces of the individual sealing members together forming a stacked subassembly inner surface; and
   a unitary core element comprising adhesive cast or molded over the stacked subassembly to encapsulate at least a portion of the stacked subassembly, the unitary core element having an interior surface extending over the stacked subassembly outer surface,
   the core element interior surface supporting the outer surfaces of the individual sealing members,
   the stacked subassembly inner surface defining a central bore for receiving a medical lead connector assembly,
   the inner surfaces of the individual sealing members forming a fluid-resistant interface with insulating structures of the lead connector assembly.

20. The connector assembly of claim 19 further comprising an overmold structure formed from a thermoplastic material, the overmold structure extending over and adhering to the unitary core element.

21. An implantable medical device connector assembly, comprising:
   a core element having an interior surface;
   an overmold structure extending over and adhering to the core element;
   a plurality of conductive members positioned along the interior surface of the core element;
   a plurality of sealing members positioned between the conductive members;
   the plurality of sealing members having an outer surface supported by the interior surface of the core element during and after formation of the overmold structure;
   wherein the plurality of conductive members and the plurality of sealing members form a bore for receiving a medical lead connector assembly.

22. An implantable medical device connector assembly comprising:
   a stacked subassembly comprising:
   a plurality of conductive members;
   a plurality of sealing members, wherein a sealing member of the plurality of sealing members is positioned between each adjacent pair of conductive members of the plurality of conductive members in the stacked subassembly;
   wherein the plurality of the conductive members and the plurality of the sealing members define a bore within the stacked subassembly adapted for receiving a medical lead connector assembly;
   a core element containing the stacked subassembly, wherein the core element comprises:
   a sleeve comprising a lumen, wherein the stacked subassembly is located within the lumen of the sleeve;
   adhesive material located in the lumen of the sleeve, the adhesive material located between an interior surface of the sleeve and the stacked subassembly, wherein the adhesive material encapsulates at least a portion of the stacked subassembly.

23. The connector assembly of claim 22 wherein the sleeve comprises at least one fill port through which the adhesive material is delivered.

24. The connector assembly of claim 22 including a plurality of positioning structures extending along the core element.

25. The connector assembly of claim 22 wherein the core element includes a plurality of windows positioned over the conductive members.

26. The connector assembly of claim 22 wherein the plurality of conductive members and the plurality of sealing members include interlocking interfacing structures.

27. The connector assembly of claim 22 wherein the bore has a diameter sized for receiving an IS4 medical lead connector assembly.

28. The connector assembly of claim 22 wherein the adhesive material of the core element comprises epoxy.

29. The connector assembly of claim 22 wherein the adhesive material of the core element comprises thermoset material.

30. The connector assembly of claim 22 further including:
an electrically conductive circuit element having a plurality of conductive traces extending through the core element and electrically coupled to the plurality of conductive members; and
an overmold structure formed from a thermoplastic material, the overmold structure extending over and adhering to the core element and at least a portion of the electrically conductive circuit element.

31. The connector assembly of claim 30 wherein the sleeve includes a plurality of apertures through which the plurality of conductive traces extend.

32. An implantable medical device connector assembly, comprising:
a plurality of conductive members and a plurality of sealing members aligned along a bore adapted for receiving a medical lead connector assembly, wherein a sealing member of the plurality of sealing members is positioned between each adjacent pair of conductive members of the plurality of conductive members, and wherein the plurality of sealing members and the plurality of conductive members comprise inner surfaces ling the bore and outer surfaces facing away from the bore; and
a core element cast or molded over the outer surfaces of the plurality of sealing members and the outer surfaces of the plurality of conductive members, the core element formed from an adhesive that encapsulates the outer surfaces of the plurality of sealing members and the outer surfaces of the plurality of conductive members.

33. The connector assembly of claim 32 including a plurality of positioning structures extending along the core element.

34. The connector assembly of claim 32 wherein the core element includes a plurality of windows positioned over the conductive members.

35. The connector assembly of claim 32 wherein the plurality of conductive members and the plurality of sealing members include interlocking interfacing structures.

36. The connector assembly of claim 32 wherein the bore has a diameter sized for receiving an IS4 medical lead connector assembly.

37. The connector assembly of claim 32 wherein the adhesive material of the core element comprises epoxy.

38. The connector assembly of claim 32 wherein the adhesive material of the core element comprises thermoset material.

39. The connector assembly of claim 32 further including:
an electrically conductive circuit element having a plurality of conductive traces extending through the core element and electrically coupled to the plurality of conductive members; and
an overmold structure formed from a thermoplastic material, the overmold structure extending over and adhering to the core element and at least a portion of the electrically conductive circuit element.

40. The connector assembly of claim 39 wherein the core element includes a plurality of apertures through which the plurality of conductive traces extend.

\* \* \* \* \*

UNITED STATES PATENT AND TRADEMARK OFFICE
CERTIFICATE OF CORRECTION

| | | |
|---|---|---|
| PATENT NO. | : 7,654,843 B2 | Page 1 of 1 |
| APPLICATION NO. | : 11/363651 | |
| DATED | : February 2, 2010 | |
| INVENTOR(S) | : Thomas J. Olson et al. | |

It is certified that error appears in the above-identified patent and that said Letters Patent is hereby corrected as shown below:

Col. 9, line 5, delete "claim 12 further" and insert in place thereof -- claim 11 further --;

Signed and Sealed this

Twenty-sixth Day of October, 2010

David J. Kappos
*Director of the United States Patent and Trademark Office*

(12) EX PARTE REEXAMINATION CERTIFICATE (9309th)
United States Patent
Olson et al.

(10) Number: US 7,654,843 C1
(45) Certificate Issued: Sep. 18, 2012

(54) CONNECTOR ASSEMBLY WITH INTERNAL SEALS AND MANUFACTURING METHOD

(75) Inventors: Thomas J. Olson, Eagan, MN (US); Andrew J. Ries, Lino Lakes, MN (US); George Patras, Greenfield, MN (US); John D. Longtin, Lake Elmo, MN (US)

(73) Assignee: Medtronic, Inc., Minneapolis, MN (US)

Reexamination Request:
No. 90/011,556, Apr. 15, 2011

Reexamination Certificate for:
Patent No.: 7,654,843
Issued: Feb. 2, 2010
Appl. No.: 11/363,651
Filed: Feb. 28, 2006

Certificate of Correction issued Oct. 26, 2010.

(51) Int. Cl.
*H01R 13/64* (2006.01)

(52) U.S. Cl. .................................. 439/248; 607/115
(58) Field of Classification Search ............... 439/668
See application file for complete search history.

(56) References Cited

To view the complete listing of prior art documents cited during the proceeding for Reexamination Control Number 90/011,556, please refer to the USPTO's public Patent Application Information Retrieval (PAIR) system under the Display References tab.

*Primary Examiner* — Kenneth J Whittington (57) ABSTRACT

A medical device connector assembly and fabrication method are provided wherein the connector assembly includes a core element, a plurality of conductive members positioned along the core element, and a pluraltiy of sealing members positioned between the conductive members, the sealing members having an outer surface supported by the core element.

US 7,654,843 C1

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 11, 12 and 22 is confirmed.

Claims 1-9, 16-21 and 32-40 are cancelled.

Claims 10, 13-15 and 23-30 are determined to be patentable as amended.

Claim 31 dependent on an amended claim, is determined to be patentable.

New claims 41-44 are added and determined to be patentable.

10. [The connector assembly of claim 9] *An implantable medical device connector assembly, comprising:*
  *a core element having an interior surface;*
  a plurality of conductive members positioned along the interior surface of the core element;
  a plurality of sealing members positioned between the conductive members;
  *the plurality of sealing members having an outer surface supported by and maintained in stable positions with respect to the conductive members by the interior surface of the core element;*
  wherein the plurality of conductive members and the plurality of sealing members form a bore;
  an electrically conductive circuit element having a plurality of conductive traces extending through the core element and electrically coupled to the plurality of conductive members; and
  an overmold structure formed from a thermoplastic material, the overmold structure extending over and adhering to the core element and at least a portion of the electrically conductive circuit element; *and*
  *wherein the core element includes a rigid sleeve; and*
  wherein the rigid sleeve includes at least one fill port through which a core element material is delivered.

13. [The method of claim 11] *A method for manufacturing an implantable medical device connector assembly, comprising:*
  stacking a plurality of individual conductive members and a plurality of individual sealing members, the individual sealing members positioned between the individual conductive members to form a stacked subassembly;
  forming a core element along at least a portion of the stacked subassembly including the plurality of individual sealing members;
  electrically coupling conductive traces to the conductive members; and
  overmolding the core element in a thermoplastic material; and
  wherein electrically coupling conductive traces to the conductive members includes performing the electrically coupling through windows included in the core element; and
  further including inserting the stacked subassembly in a sleeve and wherein forming the core element includes filling the sleeve with an adhesive.

14. [The method of claim 11] *A method for manufacturing an implantable medical device connector assembly, comprising:*
  stacking a plurality of individual conductive members and a plurality of individual sealing members, the individual sealing members positioned between the individual conductive members to form a stacked subassembly;
  forming a core element along at least a portion of the stacked subassembly including the plurality of individual sealing members;
  electrically coupling conductive traces to the conductive members; and
  overmolding the core element in a thermoplastic material; and
  wherein forming the core element comprises allowing a core element material to cure, the cured core element supporting an outer surface of the sealing members during the overmolding.

15. [The method of claim 14] *A method for manufacturing an implantable medical device connector assembly, comprising:*
  stacking a plurality of individual conductive members and a plurality of individual sealing members, the individual sealing members positioned between the individual conductive members to form a stacked subassembly;
  forming a core element along at least a portion of the stacked subassembly including the plurality of individual sealing members;
  electrically coupling conductive traces to the conductive members; and
  overmolding the core element in a thermoplastic material; and
  wherein the core element is cured at a first temperature and a first pressure and the overmolding occurs at one of a second temperature greater than the first temperature and a second pressure greater than the first pressure.

23. The connector assembly of claim 22 *or claim 44* wherein the sleeve comprises at least one fill port through which the adhesive material is delivered.

24. The connector assembly of claim 22 *or claim 44* including a plurality of positioning structures extending along the core element.

25. The connector assembly of claim 22 *or claim 44* wherein the core element includes a plurality of windows positioned over the conductive members.

26. The connector assembly of claim 22 *or claim 44* wherein the plurality of conductive members and the plurality of sealing members include interlocking interfacing structures.

27. The connector assembly of claim 22 *or claim 44* wherein the bore has a diameter sized for receiving an IS4 medical lead connector assembly.

28. The connector assembly of claim 22 *or claim 44* wherein the adhesive material of the core element comprises epoxy.

29. The connector assembly of claim 22 *or claim 44* wherein the adhesive material of the core element comprises theremoset material.

30. The connector assembly of claim 22 *or claim 44* further including:
- an electrically conductive circuit element having a plurality of conductive traces extending through the core element and electrically coupled to the plurality of conductive members; and
- an overmold structure formed from a thermoplastic material, the overmold structure extending over and adhering to the core element and at least a portion of the electrically conductive circuit element.

*41. A method for manufacturing an implantable medical device connector assembly, comprising the ordered steps of:*
- *stacking a plurality of individual conductive members and a plurality of individual sealing members, the individual sealing members positioned between the individual conductive members to form a stacked subassembly;*
- *forming a core element along at least a portion of the stacked subassembly including the plurality of individual sealing members;*
- *electrically coupling conductive traces to the conductive members; and*
- *overmolding the core element in a thermoplastic material*

*42. A method for manufacturing an implantable medical device connector assembly, comprising the ordered steps of:*
- *stacking a plurality of individual conductive members and a pluraltiy of individual sealing members, the individual sealing members positioned between the individual conductive members to form a stacked subassembly;*
- *forming a core element along at least a portion of the stacked subassembly including the plurality of individual sealing members, wherein forming the core element comprises allowing a core element material to cure, the cured core element supporting an outer surface of the sealing members during the overmolding;*
- *electrically coupling conductive traces to the conductive members; and*
- *overmolding the core element in a thermoplastic material.*

*43. A method for manufacuring an implantable medical device connector assembly, comprising the ordered steps of:*
- *stacking a plurality of individual conductive members and a plurality of individual sealing members, the individual sealing members positioned between the individual conductive members to form a stacked subassembly;*
- *forming a core element along at least a portion of the stacked subassembly including the plurality of individual sealing members,*
- *electrically coupling conductive traces to the conductive members; and*
- *overmolding the core element in a thermoplastic material; and*
- *further including inserting the stacked subassembly in a sleeve and wherein forming the core element includes filling the sleeve with an adhesive;*
- *the stacked subassembly inner surface defining a central bore for receiving a medical lead connector assembly;*
- *the inner surfaces of the individual sealing members forming a fluid-resistant interface with insulating structure of the lead connector assembly.*

*44. An implantable medical device connector assembly comprising:*
- *a stacked subassembly comprising:*
  - *a plurality of conductive members;*
  - *a plurality of sealing members, wherein a sealing member of the plurality of sealing members is positioned between each adjacent pair of conductive members of the plurality of conductive members in the stacked subassembly;*
  - *wherein the plurality of the conductive members and the plurality of the sealing members define a bore within the stacked subassembly adapted for receiving a medical lead connector assembly;*
- *a core element containing the stacked subassembly, wherein the core element comprises:*
  - *a sleeve comprising a lumen, wherein the stacked subassembly is located within the lumen of the sleeve;*
  - *adhesive material located in the lumen of the sleeve, the adhesive material located between an interior surface of the sleeve and the stacked subassembly, wherein the adhesive material encapsulates at least a portion of the stacked subassembly and maintains the sealing members in stable positions with respect to the conductive members.*

\* \* \* \* \*